(12) United States Patent
Birthisel et al.

(10) Patent No.: US 7,867,507 B2
(45) Date of Patent: Jan. 11, 2011

(54) PESTICIDE DELIVERY GRANULE

(75) Inventors: Timothy D. Birthisel, Perrysburg, OH (US); James R. Lynch, Toledo, OH (US); Matthew G. Johnston, Centennial, CO (US)

(73) Assignee: The Andersons, Inc., Maumee, OH (US)

( * ) Notice: Subject to any disclaimer, the term of this patent is extended or adjusted under 35 U.S.C. 154(b) by 169 days.

(21) Appl. No.: 11/556,290

(22) Filed: Nov. 3, 2006

(65) Prior Publication Data

US 2007/0104749 A1 May 10, 2007

Related U.S. Application Data

(60) Provisional application No. 60/733,633, filed on Nov. 4, 2005.

(51) Int. Cl.
*A01N 25/00* (2006.01)
*A01N 25/08* (2006.01)
*A01N 25/24* (2006.01)
*A01N 47/10* (2006.01)
*A01N 53/10* (2006.01)

(52) U.S. Cl. ............... 424/405; 424/410; 514/479; 514/531

(58) Field of Classification Search ........... 504/367; 424/405, 410; 514/479, 531
See application file for complete search history.

(56) References Cited

U.S. PATENT DOCUMENTS

| | | | |
|---|---|---|---|
| 3,083,089 A | 3/1963 | Renner | |
| 3,137,618 A | 6/1964 | Pearce | |
| 3,617,246 A | 11/1971 | Duyfjes et al. | |
| 3,620,453 A | 11/1971 | Gancberg et al. | |
| 3,785,798 A | 1/1974 | Horai et al. | |
| 3,849,105 A | 11/1974 | Woods | |
| 3,980,463 A | 9/1976 | Muramoto et al. | |
| 4,015,970 A | 4/1977 | Hennart | |
| 4,042,366 A | 8/1977 | Fersch et al. | |
| 4,198,397 A | 4/1980 | Gillings et al. | |
| 4,325,966 A | 4/1982 | Punja | |
| 4,834,977 A | 5/1989 | Kohama et al. | |
| 5,047,243 A | 9/1991 | Antfang et al. | |
| 5,169,644 A | 12/1992 | Mölls et al. | |
| 5,326,573 A | 7/1994 | Antfang et al. | |
| 5,346,704 A | 9/1994 | Lajoie | |
| 5,750,130 A | 5/1998 | Ferrell et al. | |
| 5,783,203 A | 7/1998 | Schütte et al. | |
| 5,830,576 A | 11/1998 | Mehra et al. | |
| 6,221,374 B1 * | 4/2001 | Ghosh et al. | 424/405 |
| 6,221,375 B1 | 4/2001 | Howse | |
| 6,387,388 B1 | 5/2002 | Misselbrook et al. | |
| 6,436,421 B1 | 8/2002 | Schindler et al. | |
| 6,514,512 B1 | 2/2003 | Puterka et al. | |
| 6,660,690 B2 * | 12/2003 | Asrar et al. | 504/100 |
| 6,858,634 B2 | 2/2005 | Asrar et al. | |
| 6,884,756 B2 * | 4/2005 | Lynch et al. | 504/101 |
| 6,890,888 B2 | 5/2005 | Pursell et al. | |
| 7,018,643 B2 | 3/2006 | Puterka et al. | |
| 2002/0047057 A1 | 4/2002 | Elliot, Jr. et al. | |
| 2002/0114821 A1 | 8/2002 | Lescota et al. | |
| 2004/0033248 A1 | 2/2004 | Pursell et al. | |
| 2005/0255251 A1 | 11/2005 | Hodge et al. | |
| 2008/0319023 A1 | 12/2008 | Richman et al. | |

OTHER PUBLICATIONS

Allectus GC Granular Insecticide, Sep. 22, 2004, Bayer Environmental Science, pp. 1-4.*
Washington State Pest Management Resource Service "Pesticide Notfication Network", http://ext.wsu.edu/pnn/user/view; Mar. 4, 2009.
Allectus, Expo here Nov. 5, 2004; LM Week in Review; "Bayer unveils new turfgrass insect control product" http://www.golfdom.com/landscape/article.
MEE vol. 2005-12; "Materials Entering Evaluation Process"; Mar. 23, 2005 vol. 2005-12; http://www.cdpr.ca.gov/docs/registration/mee/2005.
Bayer Environmental Science, "Material Safety Data Sheet"; Allectus™ G Insecticide; MSDS No. 102000011589; MSDS Version 2.0; Revision Date: Mar. 2, 2005.

* cited by examiner

*Primary Examiner*—Johann R Richter
*Assistant Examiner*—Andriae M Holt
(74) *Attorney, Agent, or Firm*—Gifford, Krass, Sprinkle, Anderson & Citkowski, P.C.

(57) ABSTRACT

A pesticide granule is provided that includes a base carrier particle. A liquid pesticide coating is applied to the particle surface. The coating may contain adjuvants. The coating has sufficient tack to adhere a second powdered pesticide to the carrier particle. The usage of tackifying agents to render the particle surface tacky enough to adhere powdered pesticide is reduced or eliminated. The powdered pesticide is sized to a mean diameter of less than 10% of the carrier diameter to promote adhesion. The synergistic rapid acting pesticide delivery associated with the granule results in the usage of less pesticide to control a given pest with reduced environmental impact. Bifenthrin is a representative of the liquid pesticide.

15 Claims, No Drawings

US 7,867,507 B2

PESTICIDE DELIVERY GRANULE

CROSS-REFERENCE TO RELATED APPLICATIONS

This application is a non-provisional application that claims priority benefit of U.S. Provisional application 60/733,633, filed Nov. 4, 2005; the contents of which are incorporated by reference.

FIELD OF THE INVENTION

The present invention relates in general to particles for simultaneous delivery of multiple pesticides and in particular to the simultaneous delivery of synergistic solid and liquid pesticides.

BACKGROUND OF THE INVENTION

With a greater appreciation as to environmental damage associated with pesticide usage, there are ever-increasing limitations as to the classes of chemical compounds suitable as pesticides as well as limitations when those pesticides can be spread on a crop. In many cases in order to ameliorate environmental damage associated with pesticide application, pesticide use is mandated during seasons when the pest lifecycle is not at the most vulnerable stage. With integrated pest management now endorsed by environmental regulatory agencies, industry associations, and entomologists, more judicious pesticide usage should be expected in the future.

An ongoing problem in minimizing pesticide usage is the difficulty in delivery of a pesticide efficiently to a target plant within a large area of cultivated vegetation. A practical laborsaving approach to pesticide delivery to such as golf courses, parks, lawns, gardens and agricultural fields has been broadcast application of granular products containing a pesticide with equipment such as a rotary spreader. Using granular products having particle sizes in the range of about 1 millimeter to about 10 millimeters, an operator can cover a large area with minimal distance traversed by the spreader itself while at the same time applying the granular pesticide with relative uniformity over the desired area. Unfortunately, such granular pesticides often remain in solid or semisolid form for a considerable time following application. Since the pesticide is typically bound physically within the granule, the pesticide efficacy is reduced or delayed, potentially resulting in a loss of active ingredient via volatilization or photodegradation.

A further consequence of granular pesticide distribution is that the granules are subject to removal by plant culture operations such as mowing or aerating, or environmental factors such as wind and rain. Unintended removal is especially problematic on sloping ground where the underlying soils have low percolation rates, where ground cover is sparse, or in areas of high foot traffic. These actions contribute to a loss of uniformity in pesticide application and therefore efficacy is altered due to excessive concentration of the product within certain treated areas while other areas suffer diminished pesticide concentrations. Additionally, a long-persistent granule creates a greater likelihood that people, beneficial insects, and animals will come into physical contact with the granules, resulting in undue adverse health effects and environmental degradation. An alternative to long-persistent granule products is spray application of a liquid pesticide. Unfortunately, spray treatments require considerable skill for application and result only in contact to exposed foliage with other surfaces receiving only indirect drainage from exposed foliage. Additionally, spray treatment tends to dissipate quickly. Due to spray atomization of liquid pesticides, a considerable amount of pesticide is lost through volatilization and wind drift and tends to be applied in greater quantities to reach pests dwelling on the underside of foliage. The net result is inefficient pesticide usage; non-target hazard effects to: people, wildlife, and non-target property. Other deleterious effects of inefficient usage of pesticides include leaching through rain contact causing environmental wastewater management issues and aerosol pollution.

Thus, there exists a need for a pesticide delivery granule that affords rapid release from a solid pesticide granule and efficient delivery of a complementary liquid pesticide.

SUMMARY OF THE INVENTION

A pesticide granule is provided that includes a base carrier particle. A liquid pesticide coating is applied to the particle surface. The coating may contain adjuvants. The coating has sufficient tack to adhere a second powdered pesticide to the carrier particle. The usage of tackifying agents to render the particle surface tacky enough to adhere powdered pesticide is reduced or eliminated. The powdered pesticide is sized to a mean diameter of less than 10% of the carrier diameter to promote adhesion. The synergistic rapid acting pesticide delivery associated with the granule results in the usage of less pesticide to control a given pest with reduced environmental impact. Bifenthrin is a representative of the liquid pesticide. A pesticide granule is applied by distribution to a target turf, ornamental plant, or other crop.

DETAILED DESCRIPTION OF THE PREFERRED EMBODIMENTS

The present invention has utility as a granule to deliver in combination a liquid pesticide and a powdered pesticide as successive coatings on a base carrier particle. The present invention has utility to deliver a pesticide for the benefit of plant culture. The use of an inventive granule achieves superior handling and efficiency of active ingredient usage as compared to the conventional art. According to the present invention, the usage of inert adhesion and dusting agents conventional to the art is eliminated or at least greatly diminished, affording ease of manufacture and higher efficacy through avoidance of unintended chemistry between inert ingredients under application conditions.

A base carrier particle operative in the present invention need only be well sized for broadcast distribution and be inert towards an overlying coating of liquid pesticide. Typically, a base carrier particle has a size from 500 to 3000 microns. Suitable carrier particles include fragmented materials such as rock dust, clay, corncob, cereal or grain hulls, peanut hulls, plant pulp, other plant-based cellulosic materials, clays, granular baits, and fertilizers. Specific examples of base carrier particles include: limestone particulate having a mean particle size of 1000 microns; blended fertilizer composed of urea, diammonium phosphate, and potassium chloride having a mean particle size of 2150 microns; processed snack food; and defatted, extruded corn granules having a mean particle size of 1500 microns. Alternatively, a carrier particle is formed through the combination of a binder component with fine grain particle as detailed above has 90% of the particles having a diameter less than 150 microns. Particulate is typically present from 0.1 to 99.9 total weight percent and preferably from 5 to 98 total weight percent. An exemplary composite carrier particle is disclosed in U.S. Pat. No. 6,884,756.

A binder component is present in a carrier particle an amount ranging from 0.1% to 75% by weight of the total dry weight of the carrier particle. In a further embodiment, the binder component is present in an amount ranging from 1% to 25% by weight of the total dry weight of the particle. A binder component is included in a particle as necessary to produce or promote cohesion in forming a particle capable of retaining a specified form during transport and/or distribution. A binder component may be bentonite clay, carbohydrate, protein, lipid, synthetic polymer, glycolipid, glycoprotein, lipoprotein, lignin, a lignin derivative, a carbohydrate-based composition, and a combination thereof. In a preferred embodiment the binder component is a lignin derivative and is optionally calcium lignosulfonate. Alternatively, the binder component is selected from the group consisting of: a monosaccharide, a disaccharide, an oligosaccharide, a polysaccharide and combinations thereof. Specific carbohydrate binders illustratively include glucose, mannose, fructose, galactose, sucrose, lactose, maltose, xylose, arabinose, trehalose and mixtures thereof such as corn syrup; celluloses such as carboxymethylcellulose, ethylcellulose, hydroxyethylcellulose, hydroxymethylethylcellulose, hydroxyethylpropylcellulose, methylhydroxyethyl-cellulose, methylcellulose; starches such as amylose, seagel, starch acetates, starch hydroxyethyl ethers, ionic starches, long-chain alkyl starches, dextrins, amine starches, phosphates starches, and dialdehyde starches; plant starches such as corn starch and potato starch; other carbohydrates such as pectin, amylopectin, xylan, glycogen, agar, alginic acid, phycocolloids, chitin, gum arabic, guar gum, gum karaya, gum tragacanth and locust bean gum; vegetable oils such as corn, soybean, peanut, canola, olive and cotton seed; complex organic substances such as lignin and nitrolignin; derivatives of lignin such as lignosulfonate salts illustratively including calcium lignosulfonate and sodium lignosulfonate and complex carbohydrate-based compositions containing organic and inorganic ingredients such as molasses. Suitable protein binders illustratively include soy extract, zein, protamine, collagen, and casein. Binders operative herein also include synthetic organic polymers capable of promoting or producing cohesion of particle components and such binders illustratively include ethylene oxide polymers, polyacrylamides, polyacrylates, polyvinyl pyrrolidone, polyethylene glycol, polyvinyl alcohol, polyvinylmethyl ether, polyvinyl acrylates, polylactic acid, and latex. In a preferred embodiment, the binder is calcium lignosulfonate, molasses, a liquid corn starch, a liquid corn syrup or a combination thereof.

Optionally, the carrier particle incorporates a fertilizer, soil nutrient, amendment material, or pest attractant. In a carrier particle incorporating a fertilizer, soil nutrient or amendment material, the fertilizer, soil, amendment material, or pest attractant is present in an amount ranging from 0.05% to 50% by weight of the total dry weight of the carrier particle. In a more preferred embodiment, the fertilizer, soil nutrient, amendment material, or pest attractant active ingredient is present in an amount ranging from 0.1% to 30% by weight of the total dry weight of the particle. In a still more preferred embodiment, the fertilizer, soil nutrient, amendment material, or pest attractant active ingredient is present in an amount ranging from 0.5% to 10% by weight of the total dry weight of the particle.

Fertilizers are substances containing one of the plant nutrients nitrogen, phosphate or potassium and illustratively include urea, sulfur-coated urea, isobutylidene diurea, ammonium nitrate, ammonium sulfate, ammonium phosphate, triple super phosphate, phosphoric acid, potassium sulphate, potassium nitrate, potassium metaphosphate, potassium chloride, dipotassium carbonate, potassium oxide and a combination of these. Soil nutrients illustratively include calcium, magnesium, sulfur, iron, manganese, copper, zinc; oxides thereof, salts thereof and combinations thereof. Amendment materials are natural organic products such as humic acid, blood meal, bone meal, seed meal, feather meal and soy meal; meat meal; animal waste from various animal sources; activated sludge, hydrolyzed animal hair; fish byproducts; chitin; composts; and a combination thereof. Pest attractants are foodstuffs, scents, or pheromones attractive to a target pest. It is appreciated that when a pest attractant is a scent or pheromone the amounts needs are quite small and typically range from 0.0001 to 0.05 total weight percent of an inventive granule. The nature of the pest attractant foodstuff, scent, or pheromone is readily selected by reviewing the existing literature as to pest diet, and sexual horomones. Representative of the literature is 'Destructive Turfgrass Insects: Biology, Diagnosis, and Control" by D. A Porter (1995).

An inventive particle is produced by a number of processes. In the preferred process, the granule components are wet-granulated through a process of steps, including mixing of various dry components, wet-massing the dry powder mixture with liquid surfactants, binders or the like, alone or with the addition of a solvent to arrive at a suitable consistency for granulating. Of the binders detailed herein, methyleneurea is particularly preferred.

Upon forming a carrier particle, a liquefied formulation of a pesticide is applied to a carrier particle surface. Preferably, the pesticide is dissolved in a solvent. Alternatively, it is appreciated that the liquid pesticide formulation is incorporated into a binder solution that promotes cohesion in the forming of the carrier particle with the proviso that the resulting carrier particle surface has sufficient tack to adhere the pesticide powder to the surface of the resulting carrier particle.

Pesticides suitable to form a liquid coating on a carrier particle, the coating being adherent towards pesticide powder simultaneously in contact with the coating in synergistic in effect therewith, include pyrethroids such as bifenthrin, permethrin, deltamethrin, lambda cyhalothrin, cyfluthrin, or betacyfluthrin; organophosphates such as chlorpyrifos; limonoids such as azadirachtin or meliartenin; phenyl pyrazoles or oxadiazines such as indoxacarb; phthalic acid diamides such as flubendiamide and anthranilic diamides. Additionally, it is appreciated that a number of conventional adjuvant systems used to solubilize a pesticide for application as a coating onto a carrier particle are rendered more effective by the present invention. By way of example, pyrethroids degrade to yield organic acids that in proximity to certain pesticide powders such as carbamates function to extend the carbamate activity half-life.

A pesticide powder adhered to a carrier particle via an intermediate coating of the liquid pesticide includes any conventional pesticide formulated as a granule or powder. Preferably, pesticide powder is sized such that the powder grain diameter has a mean particle diameter of less than 10% that of the carrier particle diameter. More preferably, the pesticide powder has a mean diameter of less than 2% that of the carrier particle diameter. Effectively, any conventional pesticide powder is operative within the present invention. Operative pesticide powders within the present invention illustratively include carbamates such as carbaryl (1-naphthyl N-methylcarbamate), neonicotinoids or nitroguanidines such imidacloprid, thiomethoxam, clothianidin or dinotefuran; diacylhydrazines such as halofenozide; neonicotines such as floconamid; organophosphates such as trichlorfon and pyrazoles such as fipronil. It is appreciated that multiple active pesticide agents are readily formulated within a pesticide powder operative herein.

Preferably, the liquid coating pesticide and powder pesticide are chosen to afford a measure of synergy in effect therebetween. Synergistic effect is noted where less of an active agent is necessary to achieve a given effect when that agent is delivered in concert with a second agent. Biological synergy is obtained when two or more pesticides are present within an inventive granule and operate on different pest species, different life stages of a pest, or act simultaneously on a single pest target.

For example, a pyrethroid controls the adult and surface-dwelling insect pests, while a carbamate controls the subsurface-dwelling insect pests. Additionally, the neurological mode of action may be selected to be complementary in result, albeit via different mechanisms. For example, a Type 1 pyrethroid such as bifenthrin produces repetitive firing of the neurons (nerve cells) by prolonging or preventing the electrochemical current flowing through the subcellular sodium channels which are necessary for proper dampening of nerve impulses in neurons. In an untreated insect, this necessary dampening occurs by "resetting" the polarity of the neuron's membrane to the polarity it had prior to the nerve impulse, which stops the neuron from firing, ending the impulse. In a similar way, a carbamate or an organophosphate acts to cause repetitive neuronal firing by a different mode of action (MOA), that being a form of acetylcholinesterase inhibition. The natural enzyme acetylcholinesterase normally serves to dampen the electrochemical transfer of a nerve impulse at the synapse, or gap, between neurons, so that a single nerve impulse is dampened down after it occurs. When the function of acetylcholinesterase is inhibited by small amounts of carbamate and/or organophosphate pesticides, the nerve often continues firing after the initial impulse. In either case, the insect is in jeopardy, since proper neuronal function directly controls insect musculature, which in turn controls critical functions like feeding, locomotion, position in the environment and breathing, for example. This repetitive firing, from any and all causations, may also lead to eventual loss of electrical excitability of the neurons, in which case that part of the nervous system shuts down entirely, often leading to the sudden death of the insect pest. The inventive combination of different MOAs is a superior approach to pest control when considering that a single pesticide functions by a single or limited number of MOAs, while the invention increases the number of MOAs operating against the pest population. Over time, pest populations may develop genetic resistance to individual pesticides by evolving some inheritable means of avoiding the effects of a single MOA, or a limited number of MOAs. The present invention increases the number of MOAs, which serves to impede the ability of a species to develop resistance. Another feature of this invention derives from the fact that pesticides like pyrethroids evoke an "avoidance behavior" in insects, via which they may survive the treatment by detecting sublethal quantities of the pesticide in the environment, and moving away to a zone of reduced concentration, which allows them to survive. The reduced reliance upon a pesticide that produces avoidance behavior allows for less overall avoidance behavior to be invoked, thereby enhancing efficacy.

The selection of the inventive components can also be made to afford a chemical synergism. For example, it is well known that carbaryl, while it is fairly efficacious and broad spectrum in its insecticidal functioning under optimal conditions, sometimes does not function well, especially if the environment has a high pH. Within the range of pH normally encountered in nature, the half-life of a carbamate pesticide varies from several hours to several days' duration; therefore it may be inconsistent in pest control. The choice of a liquid pesticide or adjuvant therefor that produces acidic degradation products in proximity to carbaryl serves to extend the carbaryl persistence half-life.

One specific example of an inventive granule having synergistic pesticide interactions includes a particle carrier coated with bifenthrin solution that in tarn adheres a carbamate powder thereto. Other active agent combinations in an inventive granule include combinations of: bifenthrin and imidacloprid; bifenthrin and halofenozide; and lambda cyahalothrin and thiamethoxam.

An inventive granule is readily formed by spray coating a liquid pesticide coating onto carrier particle being conveyed through a spray stream. Optionally, a carrier particle over coated with a liquid pesticide coating is dried for a period of time prior to introduction of a pesticide powder adherent to the liquid pesticide coating. An air mixer is particularly well suited for the adherence of pesticide powder while mitigating excessive damage to inventive granules so formed.

The usage of inventive granules entails the dispersion of granules onto turf, ornamental plantings, or any growing crops in need of prophylactic or immediate pest control. The quantity of inventive granules distributed per unit area of soil is dictated by the loading of pesticides in the inventive granules. Owing to synergistic interactions associated with the liquid and powdered pesticides coating a base carrier granule, the quantity of active pesticides applied with inventive granules is less than used through recommended for conventional application of either the liquid pesticide or powdered pesticide alone. As the following examples make clear overall pesticide usage is reduced by an amount up to and including 50 weight percent. Additional expensive tackifying agent usage is decreased or eliminated through reliance on the tackifying properties of the liquid pesticide formulation.

The present invention is further detailed with respect to the non-limiting examples which embody particular aspects of the present invention but should not be construed as a limitation on the appended claims.

EXAMPLES 1 AND 2 AND COMPARATIVE EXAMPLES 1-7

Test protocol bluegrass (*Poa pratensis*) in midsummer is divided into four-foot square test plots, the plot area being infested with Japanese beetle, European chaffer and masked chaffer pests. Each plot received a single treatment of four pounds per square meter of plot with the exception of Comparative Example 7 which is applied at three pounds per square meter. Ten weeks after application and at a time corresponding to fall in the American Midwest, the plots are evaluated for the number of white grub pests found per plot, the number of grubs per square foot and percent control. During the course of the study irrigation and rainfall were recorded. At the time of evaluation each plot contained between 0.25 and 0.38 inches of thatch. The identity of each granule applied and the percent grub control for each is noted in Table 1. Untreated control plots average 13 grubs per square foot.

TABLE 1

Percent Grub Control for Inventive Granules

| Sample | Particle Carrier | Liquid Pesticide | Powdered Pesticide | % Control |
| --- | --- | --- | --- | --- |
| Comparative Example 1 | DGLITE 150S* | 0.058 wt % Clothianidin | | 98 |

TABLE 1-continued

Percent Grub Control for Inventive Granules

| Sample | Particle Carrier | Liquid Pesticide | Powdered Pesticide | % Control |
|---|---|---|---|---|
| Comparative Example 2 | DGLITE 150S | 0.116 wt % Clothianidin | | 100 |
| Comparative Example 3 | DGLITE 150S | 0.172 wt % Clothianidin | | 100 |
| Comparative Example 4 | 80/20 XRP110 + 10+ | 0.043 wt % Bifenthrin | | 73 |
| Comparative Example 5 | Limestone** | 0.043 wt % Bifenthrin | | 43 |
| Comparative Example 6 | RH-150++ | 0.043 wt % Bifenthrin | | 45 |
| Comparative Example 7 | PNUT 110/ Limestone*** | 0.049 wt % Lambda-cyhalothrin | | 39 |
| Inventive Example 1 | DGLITE 150S | 0.058 wt % Bifenthrin | 2.3 wt % Carbaryl | 100 |
| Inventive Example 2 | DGLITE 150S | 0.029 wt % Bifenthrin | 2.3 wt % Carbaryl | 71 |

*DGLITE 150S - The Andersons line lime-based particle having average particle size of 1500 microns and produced according to U.S. Pat. No. 6,231,660 B1.
+80/20 XRP110 + 10 - Blended granulated LITE-R COBS and kiln dried dolomitic limestone with a mean particle diameter of 110 microns
**Limestone - Kiln dried dolomitic limestone with a mean particle diameter of 110 microns
++RH-150 - An experimental heavy density (65 PCF) version of DGLITE with a mean particle diameter of 110 microns
***PNUT 110/Limestone - Blended granulated peanut hulls and kiln dried dolomitic limestone with a mean particle diameter of 110 microns In Table 1 above, Examples 1 and 2 are representative of the present invention. Heretofore, conventional wisdom, derived from years of previous trials with carbaryl and bifenthrin alone, was that bifenthrin does not control grubs. Only carbaryl offers grub control, yet only at rates of active ingredient per acre which are 50 to 100% higher than those used here.

EXAMPLE 3 AND COMPARATIVE EXAMPLES 8 AND 9

To further highlight the synergy between multiple pesticide delivery within a single granule so as to use less active pesticide while achieving comparable results, Comparative Example 8 included the conventional delivery of two standalone products: Product A included 0.116% by weight bifenthrin adhered to a DGLITE 150S particle carrier applied to a loading of 174.24 pounds per acre and corresponding to the delivery of 0.2 pounds of bifenthrin per acre. The coating of DGLITE 150S particulate involved the application of 1.66 pounds of a premix containing 0.22 pounds of technical grade bifenthrin and 1.44 pounds of solvent matrix where the solvent for bifenthrin adhesion to the DGLITE particulate is paraffinic crop oil. Product B used DGLITE 150S as the particulate having 4.60 total weight percent carbaryl applied at an amount of 174 pounds per acre and corresponding to 8.02 pounds of carbaryl administered per acre. The carbaryl adhered to the particle carriers by mixing 8.1 pounds of technical grade carbaryl and 5.2 pounds of the sticking agent Indopol L-14, comprised of polybutene. With the dual application according to Comparative Example 8, effective control of surface dwelling pests and subsurface dwelling grubs is achieved according to the test process of Example 1 with a percent control of 100% for adult beetles and chaffers as well as grubs.

Comparative Example 9 combined the bifenthrin and carbaryl in the quantities used in Comparative Example 8 onto a single quantity of DGLITE particle carriers and corresponding to 0.116% bifenthrin and 4.60% carbaryl with the resulting dual pesticide loaded carrier being applied at the same 174 pounds per acre. An identical quantity of bifenthrin premix of 1.66 pounds is used as well as 8.1 pounds of carbaryl technical grade. However, owing to the particle tack associated with the bifenthrin and solvent matrix premix, only 1.74 pounds of sticking agent is used to make the dual pesticide loaded granule. 100% control is also noted for the dual pesticide granule with no reduction in the amount of bifenthrin or carbaryl applied relative to Comparative Example 8.

INVENTIVE EXAMPLE 3

A granule is prepared using DGLITE 150S as the particle carrier. The particle is coated with 0.058 total weight percent bifenthrin and 2.30% carbaryl using 0.83 pounds of the bifenthrin premix that included 0.108 pounds of technical grade bifenthrin and 0.72 pounds of the solvent matrix detailed above with respect to Comparative Example 8. After coating with the bifenthrin premix, the particle carriers are then coated with a solution containing 4.11 pounds of technical grade carbaryl and 1.05 pounds of sticking agent. Example 3 represents a 50% reduction in bifenthrin, carbaryl and solvent matrix, as compared to Comparative Examples 8 and 9. The resulting inventive granule is applied at the same 174 pounds per acre according to the test protocol detailed for Examples 1 and 2 and Comparative Examples 1-7. The resulting inventive granule likewise achieves 100% control even though the active bifenthrin and carbaryl pesticide dosings are decreased by 50%.

Patents and publications disclosed in the specification are indicative of the level of skill in the art to which the invention pertains. These patents and publications are hereby incorporated by reference to the same extent as if each individual patent or publication were incorporated by reference.

The foregoing description is illustrative of particular embodiments of the invention, but is not meant to be a limitation upon the practice thereof. The following claims, including all equivalents thereof, are intended to define the scope of the invention.

The invention claimed is:

1. A pesticide granule comprising:
    a carrier particle having a diameter of between 500 and 3000 micrometers;
    a liquid coating of bifenthrin, a solvent, and a binder component selected from the group consisting of bentonite clay, carbohydrate, protein, lipid, synthetic polymer, glycolipid, glycoprotein, lignin, a lignin derivative, and a carbohydrate-based composition, wherein said coating has sufficient tack to adhere it to the carrier particle; and
    carbaryl in powder form and sized to a mean diameter of less than 10% of the carrier diameter, wherein said carbaryl is adhered to said liquid coating;
    wherein the pesticide granule contains no other binding, tackifying or sticking agent to further adhere said liquid coating to the carrier particle or said carbaryl to said liquid coating.

2. The granule of claim 1 wherein said carrier particle is an aggregate.

3. The granule of claim 1 wherein said carrier particle further comprises an active agent selected from the group consisting of: a fertilizer, a soil enhancer, a pesticide, an herbicide, and a biostimulant.

4. The granule of claim 1 wherein said coating forms organic acids upon exposure to at least one of water, soil or sunlight.

5. The granule of claim 1 wherein said first pesticide and said second pesticide vary in mode of action against a pest.

6. The granule of claim 1 wherein said first pesticide is operative against a first lifecycle phase of a pest and said second pesticide is operative against a second lifecycle phase of the pest.

7. The granule of claim 1 wherein said carrier particle further comprises an insect attractant bait.

8. A process of inhibiting pests attacking turf, ornamental plantings, or any growing crops comprising: dispersing a plurality of granules according to claim 1 onto the turf, ornamental plantings, or any growing crops.

9. A pesticide granule comprising:
a carrier particle having a diameter of between 500 and 3000 micrometers;
a liquid coating of bifenthrin, a solvent, and a binder component selected from the group consisting of bentonite clay, carbohydrate, protein, lipid, synthetic polymer, glycolipid, glycoprotein, lignin, a lignin derivative, and a carbohydrate-based composition, wherein said coating has sufficient tack to adhere it to the carrier particle; an adjuvant present at less than 30 total weight percent of said coating; and
carbaryl in powder form and sized to a mean diameter of less than 10% of the carrier diameter, wherein said carbaryl is adhered to said liquid coating;
wherein the pesticide granule contains no other binding, tackifying or sticking agent to further adhere said liquid coating to the carrier particle or said carbaryl to said liquid coating.

10. The granule of claim 9 wherein said carrier particle is an aggregate.

11. The granule of claim 9 wherein said carrier particle further comprises an active agent selected from the group consisting of: a fertilizer, a soil enhancer, a pesticide, an herbicide, and a biostimulant.

12. The granule of claim 9 wherein said coating forms organic acids upon exposure to at least one of water, soil or sunlight.

13. The granule of claim 9 wherein said first pesticide and said second pesticide vary in mode of action against a pest.

14. The granule of claim 9 wherein said first pesticide is operative against a first lifecycle phase of a pest and said second pesticide is operative against a second lifecycle phase of the pest.

15. The granule of claim 9 wherein said carrier particle further comprises an insect attractant bait.

* * * * *